(12) United States Patent
Liang

(10) Patent No.: US 10,120,980 B2
(45) Date of Patent: Nov. 6, 2018

(54) DIAGNOSING PULMONARY EMBOLISM BY INTEGRATING PATIENT-LEVEL DIAGNOSIS AND EMBOLUS-LEVEL DETECTION

(71) Applicant: Jianming Liang, Phoenix, AZ (US)

(72) Inventor: Jianming Liang, Phoenix, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 281 days.

(21) Appl. No.: 15/114,164

(22) PCT Filed: Jan. 27, 2015

(86) PCT No.: PCT/US2015/012984
§ 371 (c)(1),
(2) Date: Jul. 26, 2016

(87) PCT Pub. No.: WO2015/113014
PCT Pub. Date: Jul. 30, 2015

(65) Prior Publication Data
US 2017/0004268 A1    Jan. 5, 2017

Related U.S. Application Data

(60) Provisional application No. 61/931,933, filed on Jan. 27, 2014.

(51) Int. Cl.
*G06F 1/00* (2006.01)
*G06F 19/00* (2018.01)
(Continued)

(52) U.S. Cl.
CPC .............. *G06F 19/345* (2013.01); *A61B 5/08* (2013.01); *A61B 5/7267* (2013.01); *A61B 6/50* (2013.01);
(Continued)

(58) Field of Classification Search
CPC ........... A61B 5/08; A61B 5/7267; A61B 6/50; A61B 6/5217; G06F 19/00; G06F 19/345; G16H 50/20
See application file for complete search history.

(56) References Cited

U.S. PATENT DOCUMENTS

2007/0189602 A1   8/2007   Rao et al.
2008/0125648 A1   5/2008   Bi et al.
(Continued)

OTHER PUBLICATIONS

Bi and Liang, "Multiple Instance Learning of Pulmonary Embolism Detection With Geodesic Distance Along Vascular Structure", IEEE Conference on Computer Vision and Pattern Recognition. IEEE, 2007, 1-8.
(Continued)

*Primary Examiner* — Edward Park
(74) *Attorney, Agent, or Firm* — Norton Rose Fulbright US LLP

(57) ABSTRACT

Improved pulmonary embolism (PE) detection may be obtained through computer aided-diagnosis. In particular, PE detection may be accomplished through patient-level diagnosis, embolus-level detection, or a combination of the two. Patient-level diagnosis operates to quickly exclude non-PE patients and dispatch PE-patients to treatment. Embolus-level detection operates to localize individual emboli to support personalized medicine via risk stratification. Multiple instance-based learning (MIBL) classification at the patient level explores the key observation that once any TP candidate of a patient is classified as positive, the patient is identified as PE positive. That is, MIBL focuses on correct classification of patients rather than individual candidates, to effectively and rapidly distinguish between PE patients and non-PE patients.

19 Claims, 4 Drawing Sheets

(51) Int. Cl.
A61B 6/00 (2006.01)
A61B 5/08 (2006.01)
A61B 5/00 (2006.01)
G16H 50/20 (2018.01)

(52) U.S. Cl.
CPC ............ *A61B 6/5217* (2013.01); *G06F 19/00* (2013.01); *G16H 50/20* (2018.01)

(56) References Cited

U.S. PATENT DOCUMENTS

| | | | | |
|---|---|---|---|---|
| 2008/0187201 | A1* | 8/2008 | Liang | G06K 9/00201 382/131 |
| 2009/0003511 | A1 | 1/2009 | Roy et al. | |
| 2009/0252394 | A1* | 10/2009 | Liang | G06K 9/00201 382/131 |
| 2011/0009764 | A1 | 1/2011 | Lanier et al. | |
| 2014/0279753 | A1* | 9/2014 | Dalessandro | G06N 99/005 706/12 |

OTHER PUBLICATIONS

Boser et al., "Training Algorithm for Optimal Margin Classifiers", Proceedings of the Fifth Annual ACM Workshop on Computational Learning Theory, 1992, 144-52.

Breiman, "Bagging Predictors", Machine Learning, 1996, 24(2):123-40.

Chartrand-Lefebvre, "Computed Tomography Angiography in the Diagnosis of Pulmonary Embolism: Interobserver Agreement", American Journal of Emergency Medicine, Jan. 2011, 29(1):118-9.

Costantino et al., "Interobserver Agreement in Computer Tomography Readings for Pulmonary Embolism", American Journal of Emergency Medicine, Jan. 2011, 29(1):119.

Costantino et al., "Interobserver Agreement in the Interpretation of Computed Tomography in Acute Pulmonary Embolism", American Journal of Emergency Medicine, Nov. 2009, 27(9):1109-11.

Dietterich et al., "Solving the Multiple Instance Problem With Axis-Parallel Rectangles", Artificial Intelligence, Jan. 1997, 89(1-2):31-71.

Freund et al, "Experiments with a New Boosting Algorithm", Machine Learning: Proceedings of the Thirteenth International Conference, 1996, 148-56.

Ho, "The Random Subspace Method for Constructing Decision Forests", IEEE Transactions on Pattern Analysis and Machine Intelligence, Aug. 1998, 20(8):832-44.

Hoeting et al., "Bayesian Model Averaging: A Tutorial", Statistical Science, Nov. 1999, 14(4):382-401.

Maron et al, "A Framework for Multiple-Instance Learning", Advances in Neural Information Processing Systems, 1998, 10:570-6.

Office of the Surgeon General (US), "The Surgeon General's Call to Action to Prevent Deep Vein Thrombosis and Pulmonary Embolism", National Heart, Lung, and Blood Institute (US), 2008, Rockville, MD, 49 pages.

Ouellette et al., "Pulmonary Embolism", Medscape.com, Jun. 22 2016, accessed Aug. 26 2016, 16 pages.

Rao et al., "Mining Medical Images", Image and Knowledge Management-CAD and Knowledge Solutions (IKM-CKS), 2009.

Society of Interventional Radiology, "Deep Vein Thrombosis Overview", Society of Interventional Radiology, accessed Aug. 26 2016, 3 pages, <http://www.sirweb.org/patients/deep-vein-thrombosis/>.

Stein et al., "Multidetector Computed Tomography for Acute Pulmonary Embolism", Current Opinion in Pulmonary Medicine, Sep. 2007, 13(5):384-8.

Stein et al., "Acute Pulmonary Embolism", Current Problems in Cardiology, Jul. 2010, 35(7):314-76.

Torbicki et al., "Guidelines on the diagnosis and management of acute pulmonary embolism: The Task Force for the Diagnosis and Management of Acute Pulmonary Embolism of the European Society of Cardiology (ESC)", European Heart Journal, Sep. 2008, 29(18):2276-2315.

Zhu et al., "1-norm support vector machines", Neural Information Processing Systems, NIPS 2003, 16:8 pages.

\* cited by examiner

DIAGNOSING PULMONARY EMBOLISM BY INTEGRATING PATIENT-LEVEL DIAGNOSIS AND EMBOLUS-LEVEL DETECTION

CROSS-REFERENCE TO RELATED APPLICATIONS

This application is a national phase application under 35 U.S.C. § 371 of International Application No. PCT/US2015/012984 filed Jan. 27, 2015, which claims the benefit of U.S. Provisional Patent Application No. 61/931,933 filed on Jan. 24, 2014, and entitled "Diagnosing Pulmonary Embolism By Integrating Patient-Level Diagnosis and Embolus-Level Detection", which are expressly incorporated by reference herein in their entirety.

FIELD OF THE DISCLOSURE

This disclosure relates to methods and apparatuses for patient diagnosis, and more particular detection and diagnosis of pulmonary embolism in patients.

BACKGROUND

Pulmonary embolism (PE) is a sudden blockage in a lung artery due to an embolus that is formed in one part of the body and travels to the lungs in the bloodstream through the heart. It is a common cardiovascular emergency with about 600,000 cases occurring annually and causing approximately 200,000 deaths in the United States. Most patients who succumb to PE do so within the first few hours following the event.

A major clinical challenge, particularly in an emergency department (ED), is to quickly and correctly diagnose patients with PE and dispatch them to the proper treatment, so that hazardous yet life-saving therapy can be prescribed appropriately. Unfortunately, PE is among the most difficult conditions to diagnose. The primary symptoms are protean and may be manifested by a number of other conditions that require different therapeutic interventions. The correct PE diagnosis may be overlooked in as many as 84% of cases, resulting in many preventable deaths.

CT pulmonary angiography (CTPA) is the current diagnostic standard for suspected PE. It reveals embolus as a dark region residing in bright vessel lumen. Each CTPA scan consists of hundreds of axial images. The interpretation of these images is complex and time consuming because of the intricate branching structure of the pulmonary arteries, the demand for specialized knowledge to distinguish PE from the various causes of cardiopulmonary pathology that may resemble PE, and a myriad of artifacts that may obscure or mimic emboli, such as flow-related artifacts, streak artifacts, lymph nodes, etc. The accuracy and efficiency of interpreting such large 3-D image datasets is further limited by human factors, such as attention span and eye fatigue. Incorrect CTPA interpretations are not infrequent in clinical practice. The number of CTPA examinations has increased by an order of magnitude over the past decade, while the rate of true positive examinations has fallen to just 5-10%. There is thus a critical need to mitigate rapidly mounting radiologist workloads and improve the efficiency and accuracy of PE diagnosis in CTPA.

BRIEF SUMMARY

Improved pulmonary embolism (PE) detection may be obtained through computer aided-diagnosis. In particular, PE detection may be accomplished through patient-level diagnosis, embolus-level detection, or a combination of the two. Patient-level diagnosis operates to quickly exclude non-PE patients and dispatch PE-patients to treatment. Embolus-level detection operates to localize individual emboli to support personalized medicine via risk stratification.

Patient-level diagnosis determines a patient is "PE negative" by a computer-aided detection (CAD) system when the system reports no CAD findings. Thus, if any CAD findings are reported to a patient, the patient is determined "PE positive" by the system. To correctly classify a patient as "PE positive," it is sufficient to classify one of its true positive (TP) candidates as positive, while it must correctly classify all false positives (FP) candidates negative. Patient-level diagnosis may be used to quickly exclude non-PE patients from PE patients by correctly classifying at least one TP candidate for each PE patient, while eliminating FP candidates for all patients, including PE and non-PE patients.

Multiple instance-based learning (MIBL) classification at the patient level explores the key observation that once any TP candidate of a patient is classified as positive, the patient is identified as PE positive. That is, patient-level MIBL focuses on correct classification of patients rather than individual candidates, to effectively and rapidly distinguish between PE patients and non-PE patients. According to one embodiment, this may be performed mathematically by adjusting a classification boundary such that a minimum of hinge errors occurred on all the TP candidates associated with each patient be zero.

According to one embodiment, a method may include receiving candidates for classification as true positives and false positives, wherein the candidates are associated with one of a plurality of groups; determining a classification boundary for the true positives and the false positives; calculating hinge errors for the received candidates based, at least in part, on the determined classification boundary; setting a portion of the calculated hinge errors to zero, wherein the portion comprises hinge errors corresponding to candidates on a false positive side of the determined classification boundary belong to a group of the plurality of groups also having candidates on a true positive side of the determined classification boundary; determining a shifted classification boundary based, at least in part, on the hinge errors after setting the portion of the calculated hinge errors to zero; and identifying as true positives the candidates on a true positive side of the shifted classification boundary.

According to another embodiment, a computer program product may include a non-transitory computer readable medium having code to perform the steps of receiving candidates for classification as true positives and false positives, wherein the candidates are associated with one of a plurality of groups; determining a classification boundary for the true positives and the false positives; calculating hinge errors for the received candidates based, at least in part, on the determined classification boundary; setting a portion of the calculated hinge errors to zero, wherein the portion comprises hinge errors corresponding to candidates on a false positive side of the determined classification boundary belong to a group of the plurality of groups also having candidates on a true positive side of the determined classification boundary; determining a shifted classification boundary based, at least in part, on the hinge errors after setting the portion of the calculated hinge errors to zero; and identifying as true positives the candidates on a true positive side of the shifted classification boundary.

According to a further embodiment, an apparatus may include memory and a processor coupled to the memory. The processor may be configured to perform the steps of receiving candidates for classification as true positives and false positives, wherein the candidates are associated with one of a plurality of groups; determining a classification boundary for the true positives and the false positives; calculating hinge errors for the received candidates based, at least in part, on the determined classification boundary; setting a portion of the calculated hinge errors to zero, wherein the portion comprises hinge errors corresponding to candidates on a false positive side of the determined classification boundary belong to a group of the plurality of groups also having candidates on a true positive side of the determined classification boundary; determining a shifted classification boundary based, at least in part, on the hinge errors after setting the portion of the calculated hinge errors to zero; and identifying as true positives the candidates on a true positive side of the shifted classification boundary.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments.

DETAILED DESCRIPTION

Figure 1:
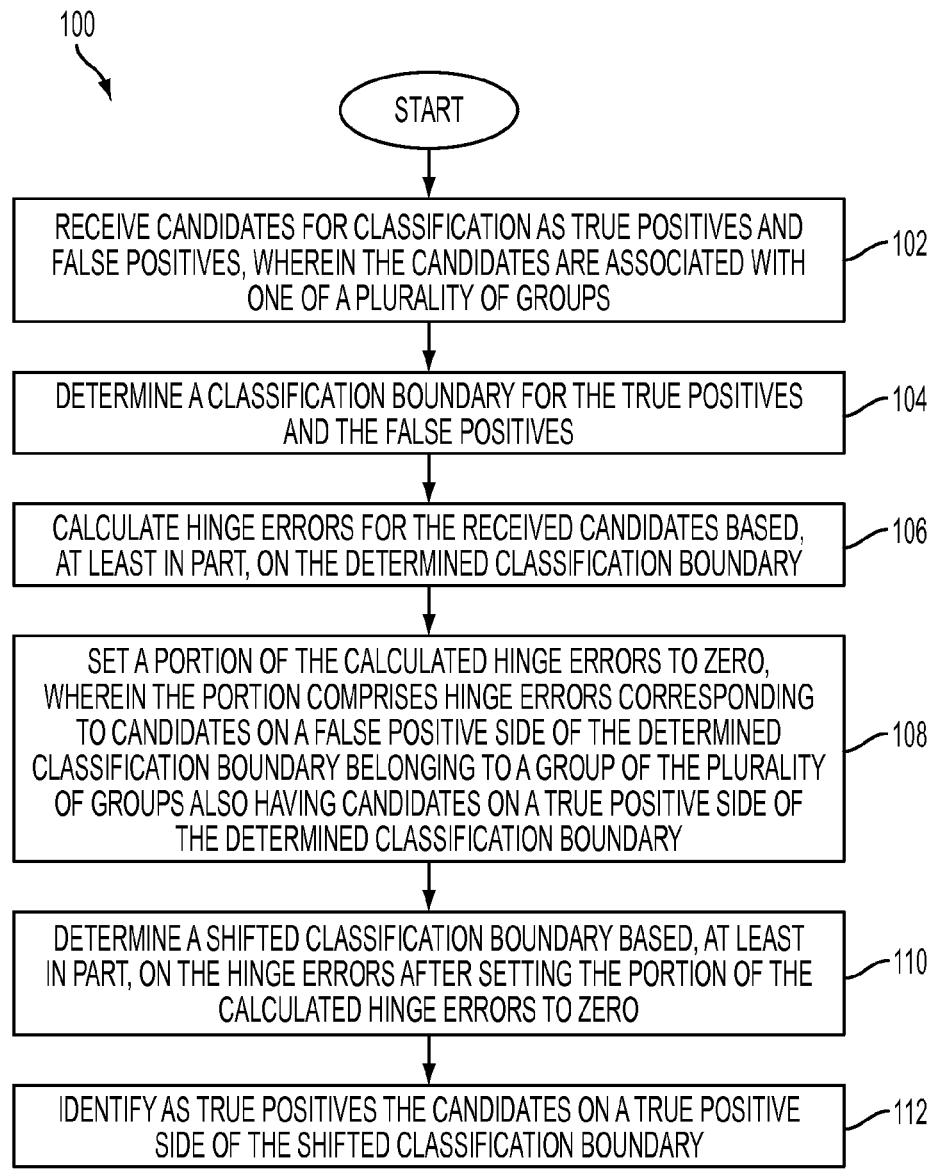
FIG. 1 is a flow chart illustrating a method of multiple instance-based learning (MIBL) for patient-level or emboli-level diagnosis according to one embodiment of the disclosure.
Figure 2A:
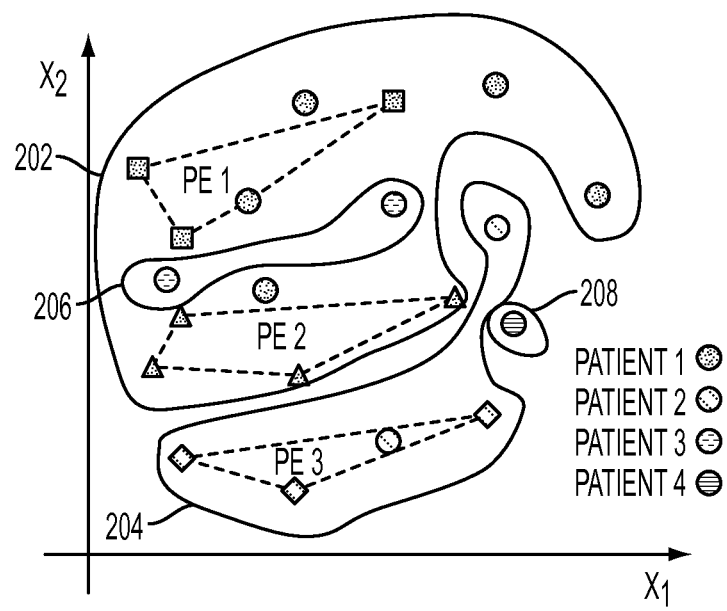
FIG. 2A is a graph illustrating an operation of method of multiple instance-based learning (MIBL) of FIG. 1 on a sample data set according to one embodiment of the disclosure.

FIG. 1 is a flow chart illustrating a method of multiple instance-based learning (MIBL) for patient-level or emboli-level diagnosis according to one embodiment of the disclosure. The method 100 begins at block 102 with receiving candidates for classification as true positives and false positives, wherein the candidates are associated with one of a plurality of groups. The plurality of groups may represent emboli or patients, depending on whether patient-level of emboli-level diagnosis is desired. The candidates may be plotted in a two-dimensional space as illustrated in FIG. 2A. A first patient may correspond to candidates 202, a second patient may correspond to candidates 204, a third patient may correspond to candidates 206, and a fourth patient may correspond to candidates 208. True positive candidates are indicated by filled in markers, and false positive candidates are indicated by hollow markers.

Figure 2B:
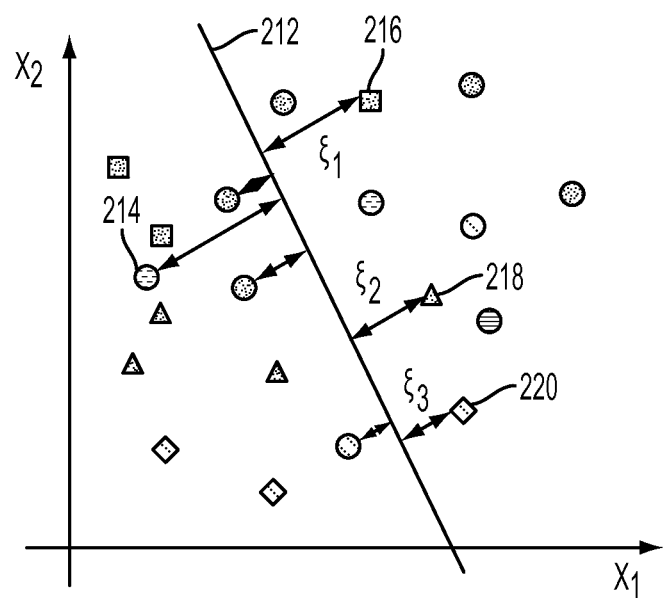
FIG. 2B is a graph illustrating an operation of method of multiple instance-based learning (MIBL) of FIG. 1 on a sample data set according to one embodiment of the disclosure.

At block 104, a classification boundary is determined for the true positives and the false positives. The classification boundary may be created by a support vector machine (SVM). At block 106, hinge errors are calculated for the received candidates based, at least in part, on the determined classification boundary. The classification boundary and the calculated hinge errors may be shown in the two-dimensional space as illustrated in FIG. 2B. However, a conventional classification boundary 212 may misclassify, for example, the third patient by placing a false positive candidate 214 on the true positive side of the classification boundary 212.

Recognizing that it is sufficient to correctly classify one TP candidate of each PE patient, some of the hinge errors may be effectively set to zero to shift the classification boundary 212. At block 108, a portion of the calculated hinge errors may be set to zero, wherein the portion comprises hinge errors corresponding to candidates on a false positive side of the determined classification boundary belong to a group of the plurality of groups also having candidates on a true positive side of the determined classification boundary. For example, hinge errors for candidates 216, 218, and 220 may be set to zero.

Figure 2C:
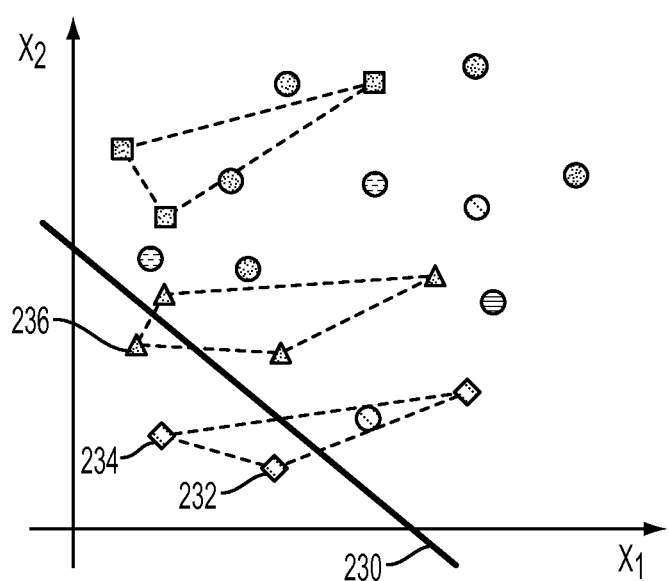
FIG. 2C is a graph illustrating an operation of method of multiple instance-based learning (MIBL) of FIG. 1 on a sample data set according to one embodiment of the disclosure.

At block 110, a shifted classification boundary may be determined based, at least in part, on the hinge errors after setting the portion of the calculated hinge errors to zero. The shifted classification boundary may be shown in the two-dimensional space as illustrated in FIG. 2C. A shifted classification boundary 230 marks only candidates 232, 234, and 236 as TP candidates.

Then, at block 112, true positives of the candidates may be identified based on their location on a true positive side of the shifted classification boundary. For example, candidates 232, 234, and 236 may be identified as true positives for pulmonary embolism. If the groups at block 102 are patients, then the patients corresponding to the candidates 232, 234, and 236 in the received set of candidates may be diagnosed with pulmonary embolism. If the groups at block 102 are emboli, then the emboli corresponding to the candidates 232, 234, and 236 in the received set of candidates may be identified as emboli.

In one embodiment, multiple classifiers may be aggregated to reduce variance in the learned classifier over different sample sets of patient images. For example, aggregation such as bagging, boosting, Bayesian averaging, and random subspace aggregation may be used to enhance classification accuracy. In an embodiment utilizing bagging for aggregation, N trials may be completed, and in each trial two-thirds of the training cases may be randomly sampled and used for training a multiple instance-based classifier by solving Equation (4) below. The remaining one-third of cases may be used for cross-validation. A linear function $f_t(x)=w_t^T x+b_t$ may be construed for a trial t. The final classifier may be based on the average model:

$$f(x) = \frac{1}{N}\sum_{t=1}^{N} f_t(x).$$

In the average model, some features may have very small weights. In some embodiments, these features' weights may be set to zero in the final aggregated classifier. The aggregated model f may then be applied to the entire training set to draw a ROC curve. A threshold a may be determined according to a desired specificity rate on the ROC curve. The patient-level classifier may then output any candidate x's that satisfy f(x)>a. The learned model and threshold may be tested on the hold-out set of test cases for evaluation.

Figure 3:
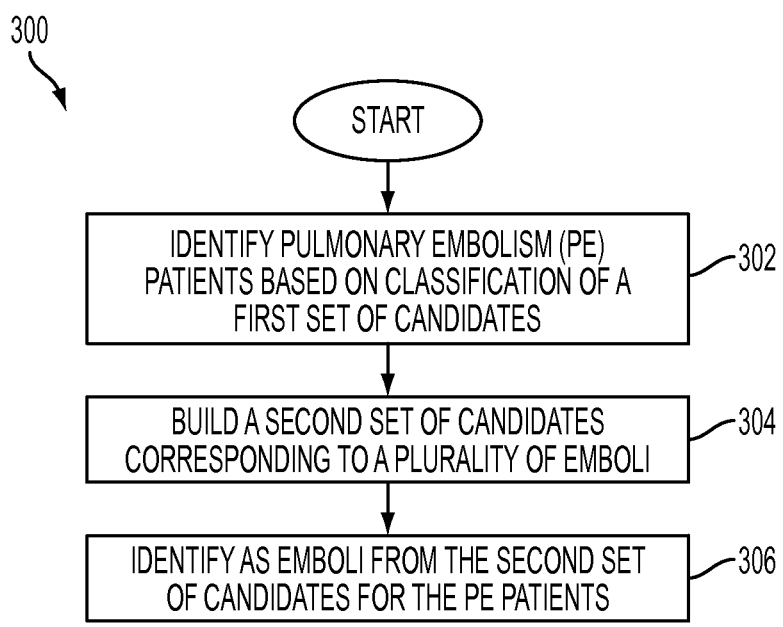
FIG. 3 is a flow chart illustrating a method of pulmonary embolism (PE) diagnosis through a combination of patient-level and embolism-level application of multiple instance-based learning (MIBL) according to one embodiment of the disclosure.

A combination of patient-level and emboli-level diagnosis may be performed to identify emboli in patients with pulmonary embolism. FIG. 3 is a flow chart illustrating a method of pulmonary embolism (PE) diagnosis through a combination of patient-level and embolism-level application of multiple instance-based learning (MIBL) according to one embodiment of the disclosure. A method 300 begins at block 302 with identifying pulmonary embolism (PE) patients based on classification of a first set of candidates. For example, block 302 may include executing the method 100 of FIG. 1 on a set of candidates corresponding to patients. At block 304, a second set of candidates corresponding to a plurality of emboli may be built. At block 306, emboli may be identified from the second set of candidates as particular emboli in the PE positive patients. Execution of block 306 may include, for example, repeating the method 100 of FIG. 1 with the set of candidates built in block 304 where the groups of block 102 correspond to emboli.

One mathematical formulation for patient-level diagnosis for use in certain embodiments of the invention described above is now presented. Assume that there are n patients, and l candidates are generated by a candidate generator, each represented by a feature vector $x_i$ associated with a label $y_i$. The label $y_i=1$ if the candidate is a true positive, otherwise $y_i=-1$. For patient p, let $I_p^+$ be a set containing indices of true positive candidates and $I_p^-$ be an index set for false positive candidates. $I_p^+$ or $I_p^-$ could be empty if there are no true positive candidates or no false positive candidates. For convenience, the following definition may be used:

$I^+=\Sigma_{p=1}^n I_p^+$, and $I^-=\Sigma_{p=1}^n I_p^-$.

Support vector machines (SVMs) may be used for classification and regression, aiming to construct linear classification functions of the form $w^T x+b$ by minimizing the hinge error defined as $\xi=\max\{0, 1-y(w^T x-b)\}$ for all candidates as written in the following optimization problem:

$\min_{w,\xi} \gamma\|w\|_1 + \Sigma_{i=1}^l \xi_i$ s.t. $y_i(w^T x_i+b)\geq 1-\xi_i$, $i=1,\ldots,l$, $\xi_i\geq 0$, $i=1,\ldots,l$. (1)

If a candidate is classified to the correct class with a margin, it receives a hinge loss $\xi=0$; otherwise, it receives a positive hinge loss. The training process involves learning a linear boundary, which minimizes the total hinge errors over all the candidates under the regularization terms. To help formulate multiple instance-based classification, Equation 1 may be rewritten by separating candidates into true positives and false positives associated each patient:

$$\min_{w,\xi} \gamma\|w\|_1 + \sum_{p=1}^{n}\left(\sum_{i\in I_P^+}\xi_i + \sum_{i\in I_P^-}-\xi_i\right) = \tag{2}$$

$$\gamma\|w\|_1 + \sum_{p=1}^{n}\sum_{i\in I_P^+}\xi_i + \sum_{p=1}^{n}\sum_{i\in I_P^-}-\xi_i = \gamma\|w\|_1 + \sum_{p=1}^{n}\sum_{i\in I_P^+}\xi_i + \sum_{i\in I}-\xi_i$$

s.t. $w^T x_i + b \geq 1 - \xi_i$, $i \in I^+$, $w^T x_i + b \leq -1 + \xi_i$, $i \in I^-, \xi_i \geq 0, i=1,\ldots,\ell.$ Multiple instance-based classification at the patient level may explore the key observation that once any TP candidate of patient p is classified as positive, patient p is identified as "PE positive." At the patient-level the focus may be on correct classification of patients rather than individual candidates, and thus facilitates the effective distinction of PE patients from non-PE patients. A geometric interpretation in a 2-D feature space is illustrated in FIG. 3.

Mathematically, distinguishing at least one TP candidate for each patient from the negative class (all FP candidates) may be equivalent to requiring that the minimum of the hinge errors ($\xi$) occurred on all the TP candidates associated with each patient be 0. In other words, in multiple-instance based learning (MIBL), what really matters for the TP candidates in each PE patient is the minimum of their hinge errors. For example, if there are 3 TP candidates in a patient and they are associated with $\xi_1=125$, $\xi_2=70$, and $\xi_3=0$, then the patient is correctly classified, because there is a candidate with no hinge error, regardless of hinge errors with other candidates. This means that the summation of the hinge errors may be replaced for all true positive candidates in Equation 2 with the summation of the minimum of hinge errors occurred on all the TP candidate associated with each patient, yielding the following optimization problem:

$\min_{w,\xi} \gamma\|w\|_1+\Sigma_{p=1}^n\min\{\xi_i, i\in I_p^+\}+\Sigma_{i\in I^-}-\xi_i$ s.t. $w^T x_i+\beta\geq 1-\xi_i$, $i\in I^+$, $w^T x_i+b\leq -1+\xi_i$, $i\in I^-$, $\xi_i\geq 0$, $i=1,\ldots,l$. (3)

To improve computation of this optimization problem, an equivalent optimization problem may be generated by introducing additional parameters $\lambda_i$:

$\min_{w,\xi,\lambda} \gamma\|w\|_1+\Sigma_{p=1}^n(\Sigma_{i\in I_p}+\lambda_i\xi_i)+\Sigma_{i\in I^-}-\xi_i$ s.t. $w^T x_i+b\geq 1-\xi_i$, $i\in I^+$, $w^T x_i+b\leq -1+\xi_i$, $i\in I^-$, $\xi_i\geq 0$, $i=1,\ldots,l$, $\Sigma_{i\in I_p^+}\lambda_i=1$, $\lambda_i\geq 0$, $i\in I_p^+$, $p=1,\ldots,n$. (4)

One mathematical formulation for embolus-level diagnosis for use in certain embodiments of the invention described above is now presented. Assume that totally l candidates are generated by a candidate generator, each represented by a feature vector $x_i$ associated with a label $y_i$. The label $y_i=1$ if the candidate is a true positive, otherwise $y_i=-1$. Let $I^+$ be a set containing indices of true positive candidates and $I^-$ be an index set for false positive candidates. Let m be the total number of embolus marked by expert radiologists in the n image datasets. Denote $I_j$ as the index set of the candidates that detect the j-th embolus, $j=1, \ldots, m$. As a result, $\cup_{j=1,\ldots,m} I_j = I^+$. Notice that $I_j \cap I_k = \emptyset$ for $j \neq k$, because there is no candidate that detects more than one embolus.

Refer to Equation 1, to help formulate multiple instance-based classification at the embolus level, the problem may be rewritten by separating candidates into true positives and false positives:

$$\min_{w,\xi} \gamma\|w\|_1 + \Sigma_{i \in I^+}\xi_i + \Sigma_{i \in I^-}\xi_i$$

s.t. $w^T x_i + b \geq 1 - \xi_i$, $i \in I^+$, $w^T x_i + b \leq -1 + \xi_i$, $i \in I^-$, $\xi_i \geq 0$, $i=1, \ldots, l$. (5)

Embolus-level detection may explore the observation that once any candidate in $I_j$ is classified as positive, the j-th embolus is identified. It focuses on correct classification of emboli rather than individual candidates, and thus facilitates the reduction of false positives by ignoring redundant "outlier" true positives when there are other true positives that can be easily classified correctly. A geometric interpretation in a 2-D feature space may be used in certain embodiments to illustrate this data.

Now, distinguishing at least one candidate for each embolus from the negative class is equivalent to requiring that the minimum of the hinge errors ($\xi$) occurred on all the candidates associated with each embolus be 0. In other words, in multiple instance-based classification, what really matters for each embolus is the minimum of hinge errors of its candidates. For example, if there are 3 candidates that detect an embolus and are associated with $\xi_1=0$, $\xi_2=5$, and $\xi_3=100$, then the embolus is correctly detected, because there is a candidate with no hinge error, regardless of hinge errors with other candidates. This means that the summation of the hinge errors for all true positive candidates in Equation 5 may be replaced with the summation of the minimum of hinge errors occurred on all the candidate associated with each embolus, yielding the following optimization problem:

$$\min_{w,\xi} \gamma\|w\|_1 + \Sigma_{j=1}^m \min\{\xi_i, i \in I_j\} + \Sigma_{i \in I^-}\xi_i$$

s.t. $w^T x_i + b \geq 1 - \xi_i$, $i \in I^+$, $w^T x_i + b \leq -1 + \xi_i$, $i \in I^-$, $\xi_i \geq 0$, $i=1, \ldots, l$. (6)

Given the great similarity of Equation 6 to Equation 3 this optimization problem may be solved by introducing additional parameters $\lambda_i$:

$$\min_{w,\xi,\lambda} \gamma\|w\|_1 + \Sigma_{j=1}^m (\Sigma_{i \in I_j}\lambda_i\xi_i) + \Sigma_{i \in I^-}\xi_i$$

s.t. $w^T x_i + b \geq 1 - \xi_i$, $i \in I^+$, $w^T x_i + b \leq -1 + \xi_i$, $i \in I^-$, $\xi_i \geq 0$, $i=1, \ldots, l$, $\Sigma_{i \in I_j}\lambda_i = 1$, $\lambda_i \geq 0$, $i \in I_j$, $j=1, \ldots, m$. (7)

Algorithmically, the difference between patient-level diagnosis and embolus-level detection is that the former finds the minimum of hinge errors among all the TP candidates of each patient (see, e.g., Equation 3 above), while embolus-level detection does so on each embolus (see, e.g., Equation 6 above). Embodiments of the MIBL described above offer a unified framework for both patient-level diagnosis and embolus-level detection. PE detection imposes a unique classification problem with several distinct aspects from the traditional multiple instance learning (MIL) problems investigated in the machine learning community. The objective of traditional MIL may be to distinguish bags, each of which may have multiple instances. This implies that labels (either positive or negative) are associated with the bags rather than their instances, and each instance exclusively belongs to a bag. The bag information may be present throughout both training and testing phases, and the bag information may be utilized by the trained classifiers during run-time. However, PE detection generally attempts to classify at least one TP candidate of a patient (or an embolus) correctly. Therefore, in the training phase, based on the ground truth provided by radiologists, which candidate belongs to which embolus and thus which patient is known. As a result, each embolus may be regarded as a bag and its candidates as instances of the bag. In some embodiments, there may be no negative bags but only negative instances (false positive candidates), even though virtual negative bags may be created by regarding each individual negative instance as a negative bag with a single instance. For PE detection, such bag information may not be not available in run-time. Therefore, a trained classifier may be independent from the bag information in testing phase and run-time. False positives may be eliminated by selectively sacrificing the redundant true PE candidates (instances in positive bags) without hurting overall detection sensitivity, even though the objective remains to classify instances rather bags.

Embodiments described above may implement multiple instance-based learning (MIBL), whereas the traditional MIL may be referred to as bag-based multiple instance learning. The MIBL embodiments described above are also applicable to the traditional MIL problems, when correctly classifying one instance in a bag implies correct classification of the bag. The proposed multiple instance-based learning described in embodiments above may also have many applications in domains other than pulmonary embolism detection.

If implemented in firmware and/or software, the functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc includes compact discs (CD), laser discs, optical discs, digital versatile discs (DVD), floppy disks and blu-ray discs. Generally, disks reproduce data magnetically, and discs reproduce data optically. Combinations of the above should also be included within the scope of computer-readable media.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present invention, disclosure, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method, comprising:
    receiving candidates for classification as true positives and false positives, wherein the candidates are associated with one of a plurality of groups;
    determining a classification boundary for the true positives and the false positives;
    calculating hinge errors for the received candidates based, at least in part, on the determined classification boundary;
    setting a portion of the calculated hinge errors to zero, wherein the portion comprises hinge errors corresponding to candidates on a false positive side of the determined classification boundary belonging to a group of the plurality of groups also having candidates on a true positive side of the determined classification boundary;
    determining a shifted classification boundary based, at least in part, on the hinge errors after setting the portion of the calculated hinge errors to zero; and
    identifying as true positives the candidates on a true positive side of the shifted classification boundary.

2. The method of claim 1, wherein the step of determining a shifted classification boundary comprises applying a support vector machine (SVM) to construct a linear classification function by minimizing the hinge errors.

3. The method of claim 2, wherein the step of constructing the linear classification function comprises constructing the linear classification function such that a minimum hinge error for candidates associated with each group of the plurality of groups is zero.

4. The method of claim 2, wherein the step of minimizing the hinge errors comprises solving the optimization problem defined by $\min_{w,\xi,\lambda} \gamma\|w\|_1 + \Sigma_{p=1}^{n}(\Sigma_{i\in I_p^+}\lambda_i\xi_i) + \Sigma_{i\in I^-}\xi_i$ s.t. $w^T x_i + b \geq 1-\xi_i, i\in I^+$, $w^T x_i + b \leq -1+\xi_i, i\in I^-$, $\xi_i \geq 0, i=1,\ldots,l$, $\Sigma_{i\in I_p}\lambda_i=1, \lambda_i\geq 0, i\in I_p^+, p=1,\ldots,n$.

5. The method of claim 2, wherein the linear classification function is of the form $w^T x+b$ and wherein the hinge error is defined as $\max\{0,1-y(w^T x-b)\}$.

6. The method of claim 1, further comprising aggregating multiple classifiers to reduce a variance of the determination of the classification boundary over multiple received candidates.

7. The method of claim 1, wherein the plurality of groups corresponds to a plurality of patients.

8. The method of claim 7, further comprising identifying a portion of the plurality of patients having a pulmonary embolism, wherein each patient of the identified portion has at least one candidate identified as a true positive.

9. The method of claim 7, further comprising:
    building a second set of candidates by selecting, from the received candidates, candidates corresponding to the portion of the plurality of patients identified as having a pulmonary embolism, wherein the second set of candidates corresponds to a plurality of emboli;
    determining a second classification boundary for the second set such that a minimum hinge error for candidates of the second set of candidates associated with each embolism of the plurality of emboli is zero; and
    identifying as true positives the candidates on a true positive side of the second classification boundary.

10. The method of claim 9, wherein the step of determining the second classification boundary comprises determining a second shifted classification boundary comprising: determining a classification boundary for true positives and false positives; calculating hinge errors for the second set of candidates based, at least in part, on the determined classification boundary; setting a portion of the calculated hinge errors to zero, wherein the portion comprises hinge errors corresponding to candidates on a false positive side of the determined classification boundary corresponding to embolisms also having candidates on a true positive side of the determined classification boundary; determining the second shifted classification boundary based, at least in part, on the hinge errors after setting the portion of the calculated hinge errors to zero.

11. The method of claim 1, wherein the plurality of groups corresponds to a plurality of pulmonary emboli.

12. A computer program product, comprising:
    a non-transitory computer readable medium comprising code to perform the steps of:
        receiving candidates for classification as true positives and false positives, wherein the candidates are associated with one of a plurality of groups;
        determining a classification boundary for the true positives and the false positives;
        calculating hinge errors for the received candidates based, at least in part, on the determined classification boundary;
        setting a portion of the calculated hinge errors to zero, wherein the portion comprises hinge errors corresponding to candidates on a false positive side of the determined classification boundary belonging to a group of the plurality of groups also having candidates on a true positive side of the determined classification boundary;
        determining a shifted classification boundary based, at least in part, on the hinge errors after setting the portion of the calculated hinge errors to zero; and identifying as true positives the candidates on a true positive side of the shifted classification boundary.

13. The computer program product of claim 12, wherein the plurality of groups corresponds to a plurality of patients.

14. The computer program product of claim 13, wherein the medium further comprises code to perform the step of identifying a portion of the plurality of patients having a pulmonary embolism, wherein each patient of the identified portion has at least one candidate identified as a true positive.

15. The computer program product of claim 12, wherein the plurality of groups corresponds to a plurality of pulmonary emboli.

16. An apparatus, comprising:
a memory; and
a processor coupled to the memory, wherein the processor is configured to perform the steps of:
receiving candidates for classification as true positives and false positives, wherein the candidates are associated with one of a plurality of groups;
determining a classification boundary for the true positives and the false positives;
calculating hinge errors for the received candidates based, at least in part, on the determined classification boundary;
setting a portion of the calculated hinge errors to zero, wherein the portion comprises hinge errors corresponding to candidates on a false positive side of the determined classification boundary belonging to a group of the plurality of groups also having candidates on a true positive side of the determined classification boundary;
determining a shifted classification boundary based, at least in part, on the hinge errors after setting the portion of the calculated hinge errors to zero; and
identifying as true positives the candidates on a true positive side of the shifted classification boundary.

17. The apparatus of claim 16, wherein the plurality of groups corresponds to a plurality of patients.

18. The apparatus of claim 17, wherein the processor is further configured to perform the step of identifying a portion of the plurality of patients having a pulmonary embolism, wherein each patient of the identified portion has at least one candidate identified as a true positive.

19. The apparatus of claim 16, wherein the plurality of groups corresponds to a plurality of pulmonary emboli.

* * * * *

UNITED STATES PATENT AND TRADEMARK OFFICE
CERTIFICATE OF CORRECTION

PATENT NO. : 10,120,980 B2
APPLICATION NO. : 15/114164
DATED : November 6, 2018
INVENTOR(S) : Jianming Liang It is certified that error appears in the above-identified patent and that said Letters Patent is hereby corrected as shown below:

<u>Claim 4, Column 9, Line 63</u>:

Delete "$+\Sigma_{p=1}{}^{n}$" and replace with --$+\Sigma_{p=1}^{n}$--

Signed and Sealed this
Twelfth Day of March, 2019

Andrei Iancu
*Director of the United States Patent and Trademark Office*